United States Patent [19]

Poole, Jr.

[11] Patent Number: 4,953,547

[45] Date of Patent: Sep. 4, 1990

[54] DRUG ADMINISTERING ENDOTRACHEAL RESPIRATION SYSTEMS

[76] Inventor: Samuel E. Poole, Jr., 6354 Saint Andrews Cir., Fort Myers, Fla. 33919

[21] Appl. No.: 301,723

[22] Filed: Jan. 26, 1989

[51] Int. Cl.$^5$ .............................................. A61B 5/08
[52] U.S. Cl. .......................... 128/203.12; 128/207.14; 128/912; 128/716; 604/283
[58] Field of Search ....................... 128/200.26, 203.12, 128/203.15, 203.16, 203.21, 207.14–207.17, 207.29, 305.3, 200, 24, 202.27, 203.25, 205.25, 911, 200.19, 716, 719; 604/283.165, 24, 54, 56, 82, 83, 85, 86, 284, 905

[56] References Cited

U.S. PATENT DOCUMENTS

| | | | |
|---|---|---|---|
| 374,831 | 12/1887 | Harrington | 128/207.14 |
| 3,633,586 | 1/1972 | Sheridan | 128/207.15 |
| 3,827,729 | 8/1974 | Kamen | 128/207.14 |
| 4,240,417 | 12/1980 | Holever | 128/203.12 |
| 4,510,933 | 4/1985 | Wendte et al. | 128/207.14 |
| 4,558,708 | 12/1985 | Labula et al. | 128/207.14 |
| 4,584,998 | 4/1986 | McGrail | 128/207.15 |
| 4,622,968 | 11/1986 | Persson | 128/200.26 |
| 4,669,463 | 6/1987 | McConnell | 128/207.14 |
| 4,681,100 | 7/1987 | Brychta et al. | 128/207.14 |
| 4,723,543 | 2/1988 | Beran | 128/202.16 |
| 4,739,756 | 4/1988 | Horn | 128/207.14 |
| 4,838,255 | 6/1989 | Lambert | 128/207.14 |
| 4,852,563 | 8/1989 | Gross | 128/912 |
| 4,852,583 | 8/1989 | Walker | 128/719 |

FOREIGN PATENT DOCUMENTS

| | | | |
|---|---|---|---|
| 3619692 | 12/1987 | Fed. Rep. of Germany | 128/200.26 |
| 8806903 | 10/1988 | PCT Int'l Appl. | 128/207.14 |

Primary Examiner—John D. Yasko
Assistant Examiner—Anthony M. Gutowski
Attorney, Agent, or Firm—Dominik, Stein, Saccocio, Reese, Colitz & Van Der Wall

[57] ABSTRACT

An improved drug administering respiration endotracheal system which permits simultaneous multiple injection of life-saving medication into the lungs of the patient without interruption of the flow of life supporting gasses. The system includes a connector with a linear axial passageway for gasses and two (2) separate medication injection ports adapted to receive a hypodermic needle and a medical syringe.

11 Claims, 1 Drawing Sheet

DRUG ADMINISTERING ENDOTRACHEAL RESPIRATION SYSTEMS

BACKGROUND OF THE INVENTION

This invention relates to endotracheal respiration systems used by paramedics, nurses, doctors, etc. to administer drugs, and more particularly, to devices for coupling endotracheal tubes to sources of gas such as air or oxygen and for allowing for the introduction of medicine while maintaining such supply of gas.

DESCRIPTION OF THE BACKGROUND ART

Conventional systems for tracheal intubation are employed routinely by health care professionals in hospital settings. The function of tracheal intubation is to provide mechanical assistance to patients for their secure of airway and respiration function. Such mechanical assistance is effected by an endotracheal tube extending from a patient's lungs to the exterior of the patient where it is coupled to a ventilation source for the administration of oxygen, air or other gasses. In hospital settings, where environmental conditions are excellent, intravenous injections are performed routinely for the most rapid administration of life-saving drugs even when a patient is being assisted by an endotracheal tube.

In pre-hospital settings, endotracheal tubes are also employed by paramedics, etc. Generally, the patient is a victim of an accident or another life-threatening medical emergency event that requires the assistance of a mechanical respiration apparatus to supplement abnormal respiration function. As in hospital settings, the preferred method of injecting life-saving drugs in emergency life-threatening situations is intravenous. Unfortunately, the use of intravenous injection of life-saving drugs in a pre-hospital setting is not always secured by I-V therapy. Hence, the alternative of intratracheal drug administration in life-threatening situations is gaining acceptance.

Current endotracheal respiration systems allow for intratracheal drug injections only after disconnecting the life-supporting ventilation apparatus supplied with oxygen. There is thus a need for an endotracheal respiration system that allows for the introduction of life-saving drugs while continuing the flow of life-supporting gasses such as air or oxygen.

Hospitals and providers of pre-hospital medicine are increasingly utilizing sterile instruments on a use-once, throw-away basis. This trend is due to the desire to reduce the transmission of hospital infection from one patient to another. Endotracheal respiration systems are in the use-once, throw-away category. The conventional endotracheal respiration system usually comprises at least two (2) separate parts: the tube and a connector for coupling to a ventilation apparatus. The parts are manufactured individually and then assembled, tested and finally packaged in a sterile container. Accordingly, the cost of the materials and labor for an endotracheal respiration system that is used only once is relatively high.

The need thus exists for an endotracheal respiration system, that is convenient, inexpensive and allows for the introduction of life-saving drugs without interrupting the flow of life-supporting gasses and that can be manufactured with few parts, assembled, tested and packaged in a sterile container for use in hospitals and prehospital settings on a use-once, throw-away basis.

Various approaches are disclosed in the literature to improve endotracheal respiration systems, including drug administering and non-drug administering endotracheal systems. By way of example. Note U.S. Pat. No. 4,739,756 issued to Horn discloses an endotracheal respiration system with a single syringe medication injection port and longitudinal bores located in the walls of the endotracheal tube to transport the medication to an ejection ring attached to the distal end of the tube.

U.S. Pat. No. 3,616,799 issued to Sparks discloses an improved seal cuff for an endotracheal tube, while U.S. Pat. No. 4,751,924 issued to Hammerschmidt et al discloses a second balloon located on the proximal end of the endotracheal tube to signal when the first balloon or cuff located on the distal end of the endotracheal tube is properly pressurized.

U.S. Pat. No. 4,700,700 issued to Eliachar discloses an inflatable cuff located on the endotracheal tube to avoid long term physical damage to the larynx, and U.S. Pat. No. 4,722,335 issued to Vilasi discloses a double wall segmented endotracheal tube that seals itself against the wall of the trachea without the need for an inflatable cuff.

Although many such advances are noteworthy to one extent or another, none achieves the objectives of an efficient, reliable, inexpensive, convenient to use drug administering endotracheal respiration system designed to accommodate the needs of a wide variety of life threatening emergency situations in various settings.

As illustrated by the great number of prior patents and known endotracheal respiration systems and drug administering techniques, efforts are continuously being made in an attempt to allow simultaneous medication injection of life-saving drugs without interrupting the flow of life supporting gasses. The printed publication Journal of Pre-hospital Medicine, Volume 2, #1, July--September, 1988, page 1, appears to disclose an endotracheal respiration system with multiple medication injection capability through a single, common medication injection port. The device, however, appears to have more parts than the present invention and also appears to allow direct intratracheal drug administration without sufficient diffusion in the gas stream of the life-supporting gasses.

None of these previous efforts, however, provides the benefits attendant with the present invention. Additionally, prior techniques do not suggest the present inventive combination of component elements as disclosed and claimed herein. The present invention achieves its intended purposes, objectives and advantages over the prior art devices through a new, useful and unobvious combination of component elements, which is simple to use, with the utilization of a minimum number of functioning parts, at a reasonable cost to manufacture, assemble, test, and by employing only readily available materials.

Therefore, the object of the present invention is to provide an improved drug administering endotracheal respiration system for administering vital life-saving drugs into the lungs of a victim while maintaining the flow of life-supporting gas thereto, the system including a gas supply; a tube for establishing gas flow exchange between the lungs of the victim and the gas supply, the tube having a proximal end and a distal end for insertion into the trachea of the victim; and an improved connector, the improved connector adapted to couple the proximal end of the tube to the gas supply, the improved connector being formed as a cylinder with a gas input end, a gas discharge end and a linear axial passageway therebetween, the connector having a hypodermic needle port adapted for receiving a hypodermic needle for injecting vital life-saving drugs in liquid form into the passageway for being atomized and then into the distal end of the tube intermixed with the gas, the improved connector further having a syringe port adapted for receiving a syringe for injecting vital life-saving drugs in liquid form into the passageway for being atomized and then into the distal end of the tube intermixed with the gas, the axial passageway adapted for atomizing and intermixing of the life-saving drugs with the flow of life-supporting gas, the ports having axes which are co-planar with respect to the axis of the connector and one port being located on the annular surface of the connector substantially 180 degrees away from the other port as measured on the annular surface of the connector, the ports being at substantially right angles with respect to its longitudinal axis of the passageway.

It is a further object of the invention to provide hospitals and providers of pre-hospital medicine an endotracheal respiration system which allows injection of life-saving drugs into the victim's lungs without interrupting the delivery of oxygen via the ventilation apparatus.

It is a further object of the present invention that the endotracheal respiration system be constructed of relatively few parts, of low cost materials which are easily fabricated, assembled, tested, and packaged in an individual sterile container for use in a use-once, throwaway setting.

It is a still further object of the present invention that the drug administering endotracheal respiration system be capable of simultaneous multiple life-saving medication injection usually found in life-threatening emergency settings such as valium for seizures, atropine for organo phosphate poisoning and/or bradyarrhythmias, epinephrine 1:10,000 for cardiac arrest, adreline 1:1,000 for anaphylaxis, lidocaine for arrhythmias and narcan for narcotic overdose, etc.

It is a further object of the present invention to atomize medicinal fluids in a flow of gas for delivery to a patient's lungs.

Finally, a still further object of the present invention is that the endotracheal respiration system not be limited to only one (1) mode of delivery, e.g., the choice of the life-saving drug should not be limited by the present methods and apparatus.

The foregoing has outlined some of the more pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention may be incorporated into an improved drug administering endotracheal respiration system for administering vital life-saving drug into the lungs of a victim while maintaining the flow of life-supporting gas thereto via ventilation apparatus comprising in combination a gas supply; a tube for establishing gas flow exchange between the lungs of the victim and the gas supply, the tube having a proximal end and a distal end for insertion into the trachea of the victim; a connector for coupling the proximal end of the tube to the gas supply, the connector being formed as a cylinder with a gas input end, a gas discharge end and a linear axial passageway therebetween, the connector having a hypodermic needle port adapted for receiving a hypodermic needle for injecting vital life-saving drugs in liquid form into the passageway and then into the distal end of the tube intermixed with the gas, the connector further having a syringe port adapted for receiving a syringe for injecting vital life-saving drugs in liquid form into the passageway and then into the distal end of the tube intermixed with the gas, the main axial passageway adapted for atomizing and intermixing of the flow of life-saving drugs with the life-supporting gas. The ports have axes which are co-planar with respect to the axis of the connector having one port located on the annular surface of the connector substantially 180 degrees away from the other port as measured on the annular surface of the connector. The connector is adapted to receive one port at a point along its longitudinal axis adjacent to the gas input end and the other port at a point along its longitudinal axis adjacent to the gas discharge end. The connector is adapted to receive the ports at substantially right angles with respect to its longitudinal axis. The connector is adapted to receive the ports at angles substantially 45 degrees with respect to its longitudinal axis. The diameter of the passageway is from about three (3) to four (4) times the diameter of each port.

The invention may also be incorporated into a system for administering vital life-saving drugs into the lungs of a victim while maintaining the flow of life-supporting gas thereto, the system including a gas supply; a tube for establishing gas flow exchange between the lungs of the victim and the gas supply, the tube having a proximal end and a distal end for insertion into the trachea of the victim; and an improved connector, the improved connector adapted to couple the proximal end of the tube to the gas supply, the improved connector being formed as a cylinder with a gas input end, a gas discharge end and a linear axial passageway therebetween, the connector having a hypodermic needle port adapted for receiving a hypodermic needle for injecting vital life-saving drugs in liquid form into the passageway for being atomized and then into the distal end of the tube intermixed with the gas, the improved connector further having a syringe port adapted for receiving a syringe for injecting vital life-saving drugs in liquid form into the passageway for being atomized and then into the distal end of the tube intermixed with the gas, the linear axial passageway adapted for atomizing and intermixing of the life-saving drugs with the flow of life-supporting gas, the ports having axes which are co-planar with respect to the axis of the connector and one port being located on the annular surface of the connector substantially 180 degrees away from the other port as measured on the annular surface of the connector, the ports being at substantially right angles with respect to its longitudinal axis of the passageway. The connector is adapted to receive the ports at angles substantially 45 degrees with respect to its longitudinal axis.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiment may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which.

Similar referenced characters refer to similar parts throughout the several Figures.

DETAILED DESCRIPTION OF THE INVENTION

Figure 1:
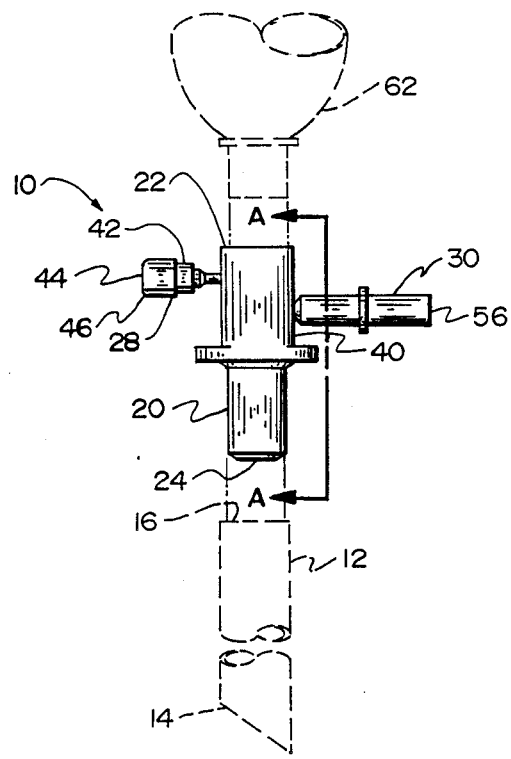
FIG. 1 is a perspective illustration of a drug administering endotracheal respiration system showing the medication injection ports in the preferred embodiment of the invention.
Figure 3:
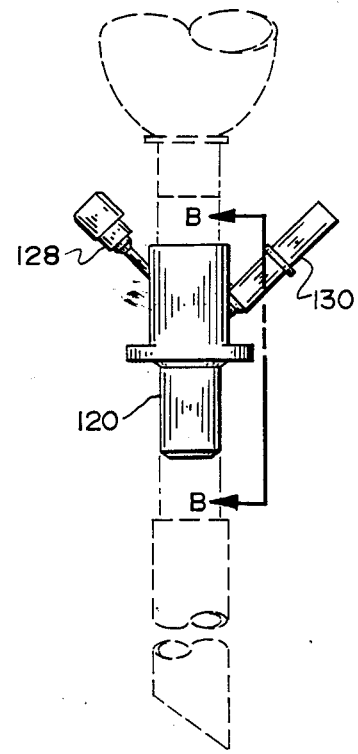
FIG. 3 is a perspective illustration of an alternative embodiment showing the medication injection ports at a forty-five (45) degree angle to the linear axial passageway.

With reference to FIG. 1, there is shown a drug administering endotracheal respiration system 10 constructed in accordance with the principles of the present invention. A tube 12 supplies life-supporting gasses and, if needed, drugs to the lungs of a victim in a life threatening emergency situation. The tube has a distal end 14 for insertion into the trachea of the patient or victim. The proximal end 16 is coupled to a connector 20. A cuff, not shown, located adjacent to distal end, is inflated after insertion by any conventional means. Although not shown, the inflatable cuff is similar to that disclosed in U.S. Pat. No. 4,600,402 issued to Rosenberg on July 15, 1986 or U.S. Pat. No. 4,700,700 issued to Eliachar on Oct. 20, 1987, which patents are hereby incorporated by reference into this application. The inflation of the cuff urges it into sealingly engagement with the inner walls of the trachea, thereby establishing gas flow communication between the lungs and the life-supporting gas supply.

The connector 20 has a gas input end 22, a gas discharge end 24, a linear axial passageway 26 therebetween, and a plurality of side ports 28 and 30. The ports extend through apertures 34 and 36 in the wall 38 of the connector 20. The connectors of the disclosed embodiments each illustrate two (2) side ports for each connector, a hypodermic needle port 28 and a syringe port 30. It can be seen that the present invention has the critical advantage of allowing the administration of life-saving drugs without interrupting the flow of life-supporting gasses. In an emergency situation, this critical advantage could be the difference between the victim arriving at the hospital alive or dead.

The hypodermic needle port 28 includes a rigid central tube 42 equipped with a rubber membrane 44 at its exterior end 46 that allows penetration by a hypodermic needle for injecting drugs. The membrane re-seals itself completely after withdrawal of the needle to eliminate leakage. This arrangement also precludes the port from becoming a potential source of bacterial infection. The interior end 48 extends into the passageway 26. Such ports are commercially available as from Abbot Hospital, Inc. as their model One/No. 5877 entitled Hep Lock.

The syringe port 30 includes a rigid central tube 50 equipped with a one-way, spring-loaded valve 54 at its exterior end that allows injection of a life-saving drug. It also re-seals itself after the syringe is withdrawn from the exterior end 56 to eliminate the problem of leakage. This arrangement also precludes the port from becoming a potential source of bacterial infection. The interior end 58 also extends into the passageway 26. Such ports are commercially available as from Itertech/Ohio, Inc. of Fort Myers, Fla. where it is utilized on endotracheal tubes for inflating balloon cuff ports.

Both ports 28 and 30 are one way ports to promote intermixing of the fluid medicines with the oxygen or other gasses. The needle port is one way via the rubber port through which the needle is advanced and retracted. The syringe port is one way via the spring loaded resealable valve triggered by the insertion and removal of the syringe.

The inner diameter of the gas input end is about 12.5 millimeters while the output end is about 6.5 millimeters. Intermediate the ends, the linear axial passageway tapers inwardly. The needle and syringe ports are formed in the side walls of the connector adjacent to the input end and have inner diameters of about two (2) to three (3) millimeters. As such, the area of the passageway is from about three (3) to four (4) times larger than the area of each port as its interior end to ensure sufficient gas flow for atomizing the administered liquid drug. The step down of the interior of the connector increases the pressure therein to promote mixing at the higher pressures and also promotes the inflation of the lungs. Such arrangement also reduces to essentially zero the possibility of air embolisms caused by other devices. The axes of the ports are parallel with each other but off-set. Such axes are coplanar with the axis of the passageway 26. The general arrangement of parts establishes fixed positions for both ports for greater accessibility by the user as compared with lengthy tubing of prior devices.

In operation and use, the paramedic, etc. inserts a tube 12 into the trachea of the emergency victim. Thereupon the cuff is inflated to insure gas flow communication between the victim's lungs and the life-supporting gas supply 62 through connector 20. The connector 12 thus couples the gas supply 62 as one end to the tube 14 at the other end. The paramedic, etc. then establishes a flow of gas, normally air or oxygen, from the source to the victim.

The paramedic, etc. then administers a life-saving drug via the hypodermic needle port 28 or syringe port 30 or both. The positive pressure in the main passageway 26 of the connector 20, supplied by the life-supporting gas supply 62, facilitates atomization or dispersion of the life-saving drug in liquid form into the flow of life-supporting gas and delivery of the medication concurrently with the gas to the lungs of the victim through the process of respiration. The paramedic, etc. is not restricted in the selection of the life-saving drug to only one (1) mode of delivery. The paramedic, etc. can choose a drug in either syringe form or hypodermic form or both. Most importantly, however, the administration of the life-saving drug can take place without interrupting the flow of life-supporting gasses.

The design of the present invention features a straight line flow of gas from the source of gas 62 to and through the connector 20, to and through the tube 12, to the victim. This design effects a rapid and direct flow of fluid, gas and medication to the victim. The medicines entering the flow of gas are at right angles to the axis of the connector and gas flow for effecting turbulence and intermixing of the medicine and the gas a rapid and efficient manner. The flow of gas also functions to create a Bernouli effect with suction to withdraw the medicines from the ports for maximum usage of the available medicine. In addition, the distal or internal ends 48 and 58 of the ports protrude into the passageway 26 and into the path of gas flow to create turbulence which promotes the intermixing of the gas and medicine. The ports being spaced within the passageway 26 extends the zone for intermixing. The ports are on opposite sides of the connector 20, spaced circumferentially one-hundred eighty (180) degrees for ease of use, separation of hypodermic needle and syringe, and for the promotion of turbulence. This is all for greater efficiency of the system.

Figure 2:
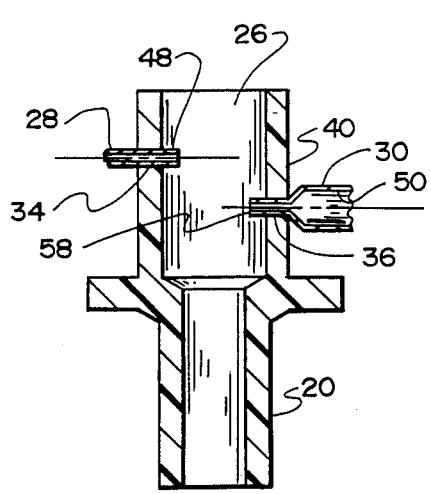
FIG. 2 is a sectional view of the connector taken along viewing line A—A.
Figure 4:
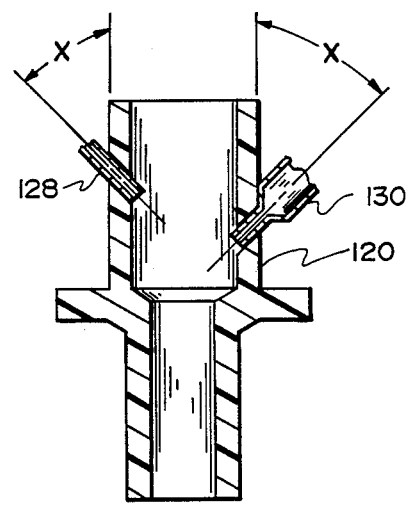
FIG. 4 is a sectional view of the alternative embodiment taken along viewing line B—B.

A second embodiment of the present invention has the hypodermic needle port 128 installed at a forty-five (45) degree angle with respect to the connector 120, rather than at ninety (90) degrees of the embodiment of FIGS. 1 and 2. The syringe port 130 is also connected to the connector 120 at a forty-five (45) degree angle. This embodiment further minimize the potential spraying of a life-saving drug from one (1) injection port across the diameter of connector to the opposite injection port. This embodiment also accelerates the injection of the life-saving drugs into the life-supporting gas stream and into the patient's lungs more rapidly due to the forty-five (45) degree angle in the direction of the patient's lungs.

The present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

Now that the invention has been described,
What is claimed is:
1. A drug administering endotracheal respiration system for administering vital life-saving drugs into the lungs of a victim while maintaining the flow of life-supporting gas thereto via ventilation apparatus comprising in combination:
    a gas supply;
    a tube for establishing gas flow exchange between the lungs of the victim and the gas supply, the tube having a proximal end and a distal end for insertion into the trachea of the victim;

a connector for coupling the proximal end of the tube to the gas supply, the connector being formed as a cylinder with a gas input end coupled to the gas supply, a gas discharge end coupled to the proximal end of the tube and a linear axial passageway therebetween, the connector having a self-sealing hypodermic needle port coupled with a first aperture in the connector and extending into the linear passageway, the hypodermic needle port being rigid and adapted for receiving a hypodermic needle for injecting vital life-saving drugs in liquid form into the passageway and then into the distal end of the tube intermixed with the gas, the connector further having a self-sealing syringe port coupled with a second aperture in the connector and extending into the linear passageway, the syringe port being rigid and adapted for receiving a syringe for injecting vital life-saving drugs in liquid form into the passageway and then into the distal end of the tube intermixed with the gas, the ports being located between the ends of the connector, and the main axial passageway adapted for atomizing and entermixing of the flow of life-saving drugs with the life-supporting gas.

2. The drug administering endotracheal respiration system as set forth in claim 1 wherein the ports have axes which are co-planar with respect to the axis of the connector.

3. The drug administering endotracheal respiration system as set forth in claim 1 wherein one port is located on the annular surface of the connector substantially 180 degrees away from the other port as measured on the annular surface of the connector.

4. The drug administering endotracheal respiration system as set forth in claim 1 wherein the connector is adapted to receive one port at a point along its longitudinal axis adjacent to the gas input end and the other port at a point along its longitudinal axis adjacent to the gas discharge end.

5. The drug administering endotracheal respiration system as set forth in claim 1 wherein the connector is adapted to receive the ports at substantially right angles with respect to its longitudinal axis.

6. The drug administering endotracheal respiration system as set forth in claim 1 wherein the connector is adapted to receive the ports at angles substantially 45 degrees with respect to its longitudinal axis.

7. The drug administering endotracheal respiration system as set forth in claim 1 wherein the diameter of the passageway is from about three (3) to four (4) times the diameter of each port.

8. The drug administering endotracheal respiration system as set forth in claim 1 wherein the needle port is a one way rubber member through which a needle is advanced and retracted.

9. The drug administering endotracheal respiration system as set forth in claim 1 and further including a conical step-down area between a larger input end and a smaller output end of the connector for increasing the pressure within the connector for the promotion of the intermixing and the lung inflation at which time drug administration takes place.

10. For use in a drug administering respiration endotracheal system for administering vital life-saving drugs into the lungs of a victim while maintaining the flow of life-supporting gas thereto via ventilation apparatus, the system including a gas supply; a tube for establishing gas flow exchange between the lungs of the victim and the gas supply, the tube having a proximal end and a distal end for insertion into the trachea of the victim; an improved connector, the improved connector adapted to couple the proximal end of the tube to the gas supply, the improved connector being formed as a cylinder with a gas input end, a gas discharge end and a linear axial passageway therebetween, the connector having a self-sealing hypodermic needle port coupled with a first aperture in the connector and extending into the linear passageway, the hypodermic needle port being rigid and adapted for receiving a hypodermic needle for injecting vital life-saving drugs in liquid form into the passageway for being atomized and then into the distal end of the tube intermixed with the gas, the improved connector further having a self-sealing syringe port coupled with a second aperture in the connector and extending into the linear passageway, the syringe port being rigid and adapted for receiving a syringe for injecting vital life-saving drugs in liquid form into the passageway for being atomized and then into the distal end of the tube intermixed with the gas, the axial passageway adapted for atomizing and intermixing of the life-saving drugs with the flow of life-supporting gas, the ports being located between the ends of a connector and having axes which are co-planar with respect to the axis of the connector and one port being located on the annular surface of the connector substantially 180 degrees away from the other port as measured on the annular surface of the connector, the ports being as substantially right angles with respect to its longitudinal axis of the passageway.

11. The drug administering respiration endotracheal system as set forth in claim 10 wherein the connector is adapted to receive the ports at angles substantially 45 degrees with respect to its longitudinal axis.

\* \* \* \* \*